United States Patent [19]
Dallas et al.

[11] Patent Number: 5,633,381
[45] Date of Patent: May 27, 1997

[54] (Z,Z), (Z,E) AND (E,Z) ISOMERS OF SUBSTITUTED BIS(PHENYLMETHYLENE) CYCLOKETONES

[75] Inventors: Jerry L. Dallas, Napa; William J. Guilford, San Leandro; Sunil K. Koovakkat, Hercules; Michael M. Morrissey, Danville; Kenneth J. Shaw, San Rafael, all of Calif.

[73] Assignee: Berlex Laboratories, Inc.

[21] Appl. No.: 270,288

[22] Filed: Jul. 5, 1994

[51] Int. Cl.$^6$ ............... A61K 31/445; C07D 211/30
[52] U.S. Cl. ............... 546/189; 549/28; 549/425; 568/329; 568/308
[58] Field of Search ............... 546/189; 549/28, 549/425; 568/329.8; 514/676, 631, 330, 432, 459, 460

[56] References Cited

U.S. PATENT DOCUMENTS 4,325,958  4/1982  Rovnyak ............... 542/441
4,341,797  7/1982  Rovnyak.

OTHER PUBLICATIONS

Walsmann et al., "Synthetic Inhibitors of Serine Proteinases," Acta. Biol. Med. Germ35 K1–K8, 1976.
Tetrahedron Letters 1971, No. 43, 4057–4060.
Thrombosis Research 1976, vol. 9, 637–646.
Acta Biol. Med. Germ. vol. 35, K1–K8.
Pharmazie 1977, No. 3, 141–145.
Haemostasis 1978, vol. 7 170–176.
Pharmazie 1978, No. 9, 599–602.
Pharmazie 1979, No. 12, 785–787.
Thrombosis Research 1980, vol. 17, 545–548.
Thrombosis Research 1989, vol. 54, 245–252.
Thrombosis and Haemostasis 1990, vol. 63, No. 2, 220–223.
Current Opinion in Therapeutic Patents, Aug. 1993.
H. George, et al., Tetrahedron Letters, "Photoisomerization and cyclo–1–2 addition of α,β–unsaturated cyclic ketones [Photoisomerisierung und 1,2,–Cycloaddition α, β–ungesättigter Cyclanonen]", vol. 43, pp. 4057—4060 (1971).
J. Stürzebecher, et al., Thrombosis Research, "Synthetic Inhibitors of Serine Proteinases XIV.[+)]Inhibition of Factor Xa by Derivatives of Benzamidine", vol. 9, pp. 637–646 (1976).
P. Walsmann, et al., Acta Biol. Med. Germ.. "Synthetic Inhibitors of Serine Proteases [Synthetische Inhibitoren der Serinproteinasen]", vol. 35, pp. K1–K8 (1976).

G. Wagner, et al., Pharmazie, "Synthesis of α,α'–bis (amidinobenzylidene) cycloakanones and α,α'–bis (amidinobenzyl) cycloalkanones [Synthese von α,α'–Bis [amidinobenzyliden] und α,α'–Bis [amidinobenzyl] cycloalkanonen]", vol. 32, No. 3, pp. 141–145, (1977).

J. Dieter Geratz, et al., Haemostasis, "Current Concepts on Action of Synthetic Thrombin Inhibitors[1],", vol. 7, pp. 170–176 (1978).

J. Stürzebecher, et al., Pharmazie, "Synthetic Inhibitors of Serine Proteinases 17$^{th}$ Communication: Effect of Benzamidine Derivatives on the Activity of Urokinase and the Course of Fibrinolysis [Synthetische Inhibitoren der Serinproteinasen 17, Miteilung: Einfluss von Benamidindervaten auf die Aktivität der Urokinase und den Ablafuf der fibrinolyse]", vol. 33, No. 9, pp. 599–602 (1978).

H. Vieweg, et al., Pharmazie, "Synthesis of α,α'–bisbenzylidenecycloalkanones with one Amidino Functional Group [Synthese von α,α'–Bisbenzylidencycloalkanonen mit einer Amidinofunktion]", vol. 34, No. 12, pp. 785–787 (1970).

J. Stürzebecher, et al., Thrombosis Research, "Synthetic Inhibitors of Proteinases XXIII. inhibition of Factor Xa By Diamidines", vol. 17, pp. 545–548 (1980).

J. Stürzebecher, et al., Thrombosis Research, "Synthetic Inhibitors of Bovine Factor Xa and Thrombin Comparison of their Anticoagulant Efficiency", vol. 54, pp. 245–252 (1989).

J. Hauptmann, et al., Thrombois and Haemostasis, "Comparison of the Anticoagulant and Antithrombotic Effects of Synthetic Thrombin and Factor Xa Inhibitors", vol. 63, pp. 220–223 (1990).

R. B. Wallis, Cardiovascular & Renal—Patent Update, "Inhititors of Coagulation Factor Xa: From Macromolecular Beginnings to Small Molecules", pp. 1173–1179 (Aug. 1993).

Primary Examiner—Porfirio Nazario-Gonzalez
Assistant Examiner—Dwayne C. Jones
Attorney, Agent, or Firm—Elizabeth A. Bellamy; Carol J. Roth; Diana Hamlet-King

[57] ABSTRACT

This invention relates to novel (Z,Z), (Z,E) and (E,Z) olefin isomers of substituted benzylidene cycloketones and their pharmaceutically acceptable salts. The compounds of the invention are potent factor Xa inhibitors thereby acting as anticoagulants useful in a number of thrombotic disease states. Pharmaceutical compositions are proposed for the compounds.

23 Claims, No Drawings

(Z,Z), (Z,E) AND (E,Z) ISOMERS OF SUBSTITUTED BIS(PHENYLMETHYLENE) CYCLOKETONES

SUMMARY OF THE INVENTION

This invention relates to novel compositions of matter, to methods for their production and to their use as anticoagulants directed against thrombotic diseases. Specifically, this invention relates to a number of (Z,Z)-, (Z,E)- and (E,Z)-olefin isomers of substituted benzylidene cycloketones and their pharmaceutically acceptable Salts as potent and selective Factor Xa inhibitors. Thus, these compounds can be directed against a host of thrombotic diseases. Further, this invention describes pharmaceutical compositions comprising said compounds and to methods for their use in treating various thrombotic diseases.

GENERAL DESCRIPTION OF THE INVENTION COMPOSITION-OF-MATTER ASPECT

In its composition-of-matter aspect, this invention relates to novel Factor Xa inhibitors and their pharmaceutically acceptable salts.

Compounds encompassed by the invention are of the following formulae I and II

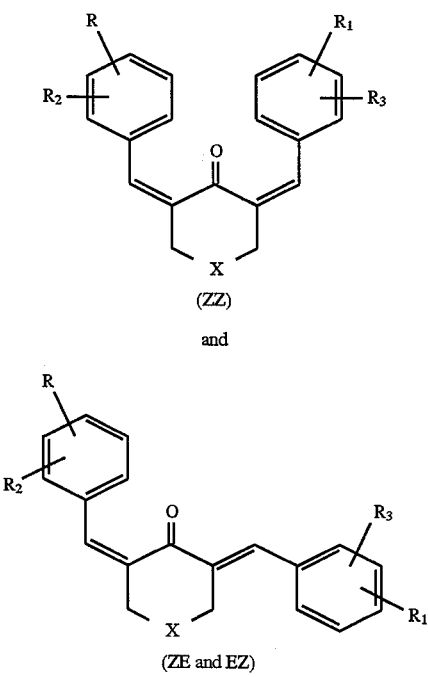

wherein $R$, $R_1$ are the same or independently

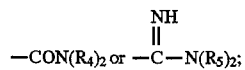

$R_2$, $R_3$ are the same or independently hydrogen, loweralkyl or halogen;

$R_4$ are the same or independently hydrogen, loweralkyl, aryl or arylloweralkyl;

$R_5$ are the same or independently hydrogen, loweralkyl, aryl, arylloweralkyl

$R_6$ is loweralkyl, aryl or arylloweralkyl;

$X$ is $(CHR_7)_n$, O, S, SO, $SO_2$ or $NR_8$;

$R_7$ is independently hydrogen, —COOH or $(-CH_2)_p-$COOH;

$R_8$ is hydrogen, loweralkyl, arylloweralkyl or

$Y$ is loweralkyl or aryl;

$n$ is the integers 1, 2, 3, 4 or 5;

$p$ is the integers 1, 2, 3 or 4 and the pharmaceutically acceptable salts thereof;

with the provisos:
a) Both $R$ and $R_1$ must be in the meta or para positions,
b) $R$ and $R_1$ cannot both be $-CON(R_4)_2$,
c) only one of $R_5$ can be

and
d) only one of $R_7$ can be —COOH or $(-CH_2)_p-$COOH.

Also considered as part of this invention are the pharmaceutically acceptable salts of the compounds of Formulae I & II. These salts may be formed with inorganic or organic acids. Illustrative but not restrictive examples of such acids include hydrochloric, hydrobromic, sulfuric, phosphoric, citric, methanesulfonic, 2-hydroxyethanesulfonic, toluenesulfonic, benzenesulfonic, camphorsulfonic, ethanesulfonic, acetic, propanoic, succinic, malic, maleic, adipic, lactic, tartaric, salicylic, and trifluoroacetic acids.

As used herein the term "halogen" shall mean fluorine or chlorine. The term lower alkyl shall refer to a straight or branched chain alkyl of one to four carbon atoms as for example, methyl, ethyl, propyl, isopropyl, butyl, sec-butyl, isobutyl and tertiary butyl. The term aryl shall refer to phenyl or napthyl (the latter attached in the α or β position). The term arylloweralkyl shall refer to the aforementioned aryl at the omega position of a one to four carbon straight chain as for example benzyl, phenylethyl, phenylpropyl, phenylbutyl, etc.

It is also to be understood that the definition of the compounds of Formula I & II encompasses all possible polymorphic modifications and other solid state modifications which possess the indicated activities.

In Formula II where $R$ and $R_1$ are the same and in the same position and both $R_2$ and $R_3$ are the same, and in the same position, only one isomer is possible and can be assigned a Z,E configuration. When, however, $R$ and $R_1$ are different and/or $R_2$ and $R_3$ are different, the compound may exist in the E,Z and Z,E configuration. These compounds are considered to be included in this invention.

The more preferred compounds are those in Formulae I & II wherein $R$, $R_1$ are in the para position.

The most preferred compounds are those described above which are in the Formula I or (Z,Z) configuration.

The compounds which follow are some of those which serve to exemplify the various composition-of-matter aspects of Formulae I & II.

a) Z,Z-4,4'-[(4-Oxo-2H-thiopyran-3,5(4H,6H)diylidene) dimethylidyne]-bis[benzenecarboximidamide]

b) Z,E-4,4'-[(4-Oxo-2H-thiopyran-3,5(4H,6H)diylidene) dimethylidyne]-bis[benzenecarboximidamide]

c) Z,Z-4,4'-[(4-Oxo-2H-thiopyran-3,5(4H,6H)diylidene) dimethylidyne]-bis[methylbenzenecarboximidamide]

d) Z,E-4,4'-[(4-Oxo-2H-thiopyran-3,5(4H,6H)diylidene) dimethylidyne]bis[methylbenzenecarboximidamide]

e) Z,Z-4,4'-[(4-Oxo-2H-pyran-3,5(4H, 6H)diylidene) dimethylidyne]bis[benzenecarboximidamide]

f) Z,E-4,4'-[(4-Oxo-2H-pyran-3,5(4H, 6H)diylidene) dimethylidyne]bis[benzenecarboximidamide]

g) Z,Z-3,3'-[(4-Oxo-2H-pyran-3,5(4H, 6H)diylidene) dimethylidyne]bis[benzenecarboximidamide]

h) Z,E-3,3'-[(4-Oxo-2H-pyran-3,5(4H, 6H)diylidene) dimethylidyne]bis[benzenecarboximidamide]

i) Z,Z-4,4'-[(4-Oxo-piperidylidenyl)dimethylidyne]bis [benzenecarboximidamide]

j) Z,E-4,4'-[(4-Oxo-piperidylidenyl)dimethylidyne]bis [benzenecarboximidamide]

k) Z,Z-3,3'-[(4-Oxo-ethylpiperidylidenyl)dimethylidyne] bis[benzenecarboximidamide]

i) Z,E-3,3'-[(4-Oxo-ethylpiperidylidenyl)dimethylidyne] bis[benzenecarboximidamide]

PROCESS ASPECTS

In general the starting materials of this invention are known compounds which are in the E,E configuration. The novel compounds of this invention are the Z,Z, Z,E and E,Z isomers of the starting materials.

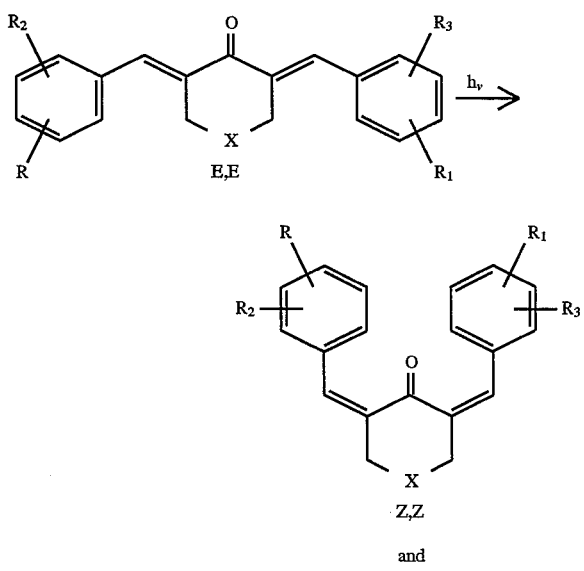

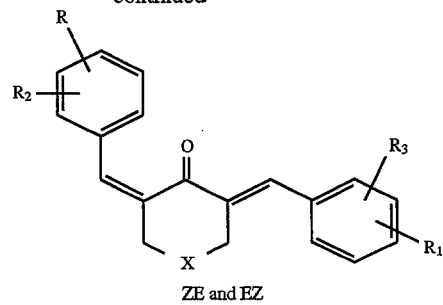

ZE and EZ wherein R, $R_1$, $R_2$, $R_3$ and X are as previously defined. Starting materials wherein X is O, S, SO, $SO_2$ and $NR_6$ can be prepared via the methods in U.S. Pat. No. 4,325,958 and starting materials wherein X is $(CHR_7)_n$ may be prepared via the methods of Wagner, et al. —Pharmazie, Vol. 32, Pages 141–145 (1977) and U.S. Pat. No. 4,341,797.

In general the novel compounds of the invention are prepared as follows:

6.24 mmol of the appropriate cycloketone compound e.g. cycloheptanone is added to a suspension of 12.24 mmol of the appropriate aldehyde in 12 ml of 85% phosphoric acid. The mixture is heated for 3 h at 100° C., then cooled to room temperature. The reaction mixture is diluted with methanol or a methanol-ether mixture, and the product that separates is filtered, and washed with methanol/ether (1:1). The crude product is suspended in methanol and treated with anhydrous HCl gas for 5 min. The solution is allowed to cool and the product is precipitated by allowing to stand or by the addition of ether to afford the EE isomer as the dihydrochloride salt.

0.40 g of the above compound is dissolved in methanol (250 mL) and irradiated with a medium pressure, quartz, mercury-vapor lamp for 3 h. The methanol is removed with a rotoevaporator, and the residue purified by preparative reverse phase HPLC, eluting with a gradient of acetonitrile (0.1% TFA)/water (0.1% TFA). In this way, all possible isomers can be separated, and lyophilization affords the isomers as their ditrifluoroacetate salts.

METHOD-OF-USE AND PHARMACEUTICAL COMPOSITION ASPECTS

The compounds of this invention are potent and selective inhibitors of the coagulation enzyme Factor Xa and thus would be useful therapeutic agents, primarily as orally active anticoagulants directed against a host of thrombotic diseases.

In a clinical setting there are a number of thrombotic diseases in clinical situations in which a safe and effective anticoagulant would be useful. For instance, prophylaxis for the long term after a myocardial infarct (MI); prophylaxis following a stroke; prophylaxis for the short term risk of deep vein thrombosis (DVT) following orthopedic surgery (e.g., knee, hip); prophylaxis of selected patients following transient ischemia attack (TIA), prophylaxis following surgical intervention such as coronary artery bypass graft (CABG) and percutaneous transluminal coronary angioplasty (PTCA). An oral anti-coagulant with reliable efficacy, safety and lack of side effects would allow aggressive treatment of thrombotic complications associated with acute promyelocytic leukemia (APL), diabetes, multiple myeloma, disseminated intravascular coagulation (DIC) associated with septic shock, purpura fulminans associated with infection, adult respiratory distress syndrome (ARDS), unstable angina, and thrombotic complications associated with aortic valve or vascular prosthesis.

Today, the treatment of the above referenced thrombotic diseases is pretty well limited to the clinical use of coumarins (e.g. warfarin) and heparin —(more recently low molecular weight fractions (LMWF) of the latter). The coumarins are orally effective but take 48 hours to become so. Dosing varies greatly from patient to patient with titration of the patient being mandatory in order to avoid a bleeding state. Heparin and its LMWF show great interpatient variability plus having the marked disadvantage of having to be given parenterally which necessitates frequent and painful injections. The types of improvements that may be made over the above agents is predictability of clinical effect, rapidity of onset of action and finally and most importantly oral availability. This last attribute avoids injections, encourages self-administration and improves efficacy.

The enzyme that converts prothrombin to thrombin, a causative agent in thrombosis, is Factor Xa. The compounds of the present invention have been shown to be potent and selective inhibitors of Factor Xa, and therefore would be useful in the treatment of thrombotic diseases.

The compounds of the invention wherein X is O, S, SO, $SO_2$ or $NR_8$ are known - but in their E,E form and as anti-inflammatory agents. The parents of the compounds of this invention wherein X is $(CHR_7)_n$ with an EE configuration are known and as Factor Xa inhibitors. What could not be foreseen was the surprisingly and inordinate differences, in activity between the EE and their isomeric Z,Z, Z,E and E,Z moieties.

There are a number of tests which illustrate the activity of the compounds of this invention. Due to the light sensitivity of the test Compounds, experiments were performed under minimally lighted conditions. The tests follow.

ASSAY OF FREE FACTOR XA AND THROMBIN

Activity of Factor Xa and thrombin (IIa) were determined as the initial rate of cleavage of peptide p-nitroanilide by the enzymes. Assays were performed in the presence or absence of inhibitors in 50 mM Tris-HCl, pH 7.5, 150 mM NaCl, 2.5 mM $CaCl_2$, 0.1% polyethylene glycol 6000, 164 µM S-2222, 3 nM HFXa (or 360 µM S-222, 3 nM rat FXa) or 300 µM S2302 and 20 nM thrombin. Reaction rate was measured at 405 nM at room temperature for 5 minutes at 10 seconds intervals. Initial rate of the first 2 minutes was used for calculation of the enzyme activities. $IC_{50}$ of the inhibitors was determined with the log-logit plots and $K_i$ for the competitive inhibitors was obtained by dividing the $IC_{50}$ by $(1+[S]K_m)$.

The results are reported in the following Table I:

TABLE I

| | Ki (nM) | |
|---|---|---|
| COMPOUND | FXa | THROMBIN |
| EX. 1 E,E | 16500 ± 800 | 6200 ± 530 |
| EX. 2 Z,Z | 1.12 ± 0.28 | 525 ± 0 |
| EX. 2 Z,E | 201 ± 57 | 132 ± 2 |
| EX. 3 E,E | 5650 ± 350 | 2970 ± 480 |
| EX. 4 Z,Z | 28.9 ± 7.0 | 1340 ± 370 |
| EX. 4 Z,E | 422 ± 167 | 115 ± 71 |
| EX. 5 E,E | >>5000 | >>5000 |
| EX. 6 Z,Z | 52.1 ± 2.5 | 107 ± 2 |

TABLE I-continued

| | Ki (nM) | |
|---|---|---|
| COMPOUND | FXa | THROMBIN |
| EX. 6 Z,E:E,Z | 1850 ± 10 | 380 |
| EX. 7 E,E | 29,000 | 12900 |
| EX. 8 Z,Z | 12.3 ± 1.8 | 1580 ± 290 |
| EX. 8 Z,E:E,Z | 504 ± 44 | 363 ± 19 |
| EX. 10 Z,Z | 17.8 ± 2.6 | 1390 ± 140 |
| EX. 11 Z,Z | 29.1 ± 5.8 | 120000 ± 7000 |
| EX. 12 E,E | 1390 ± 210 | 2140 ± 150 |
| EX. 13 Z,Z | 5.63 ± 1.97 | 1360 ± 500 |
| EX. 13 Z,E | 143 ± 38 | 1000 ± 30 |
| EX. 14 Z,Z | 111 ± 2 | 741 ± 161 |
| EX. 14 Z,E | 509 ± 26 | 146 ± 27 |
| EX. 15 Z,Z | 13.7 ± 5.5 | 619 ± 193 |
| EX. 15 Z,E | 128 ± 25 | 198 ± 18 |
| EX. 16 Z,Z | 6.0 ± 2.8 | 527 ± 52 |
| EX. 16 Z,E | 324 ± 48 | 347 ± 35 |

COAGULATION ASSAYS

Two coagulation assays, the activated partial thromboplastin time (APTT) and the prothrombin time (PT), were used to evaluate the compounds. An Electra 900C coagulometer with the software package was used. The Actin Reagent (APTT) or Rabbit Brain Thromboplastin (PT) is added to citrated plasma sample in equal volumes (100 µL each) and allowed to incubate for 5 min. at 37° C. 20 nM $CaCl_2$ (100 µL) is added and time to clot noted. Dilution series for compounds undergoing testing were made in human plasma prior to assay. The results follow in Table II:

TABLE II

| COMPOUND | APTT | PT |
|---|---|---|
| EX. 1 E,E | 17.5 | >30 |
| EX. 2 Z,Z | 0.3 | 0.3 |
| EX. 2 Z,E | 1.6 | 3.2 |

(Dose of compound µg/ml required to produce a 2 fold increase in clot time)

IN VITRO PLASMA MATRIX EFFECT ON ANTI-FX ACTIVITY:

Compound stock solutions (10 mM in DMSO) were diluted in 100% rat plasma in a series of 1 to 3 dilutions in the following concentration ranges: (1) from 300 µM to 1.23 µM; (2) from 10 µM to 0.041 µM; (3) from 100 µM to 0.412 µM. After 30 minutes incubation (in dark) at room temperature, 20 µL of diluted compounds (in rat plasma) were added in duplicate to a 96-well flat-bottom microtiter plate (Dynatech Laboratories, USA). Thirty microliter of assay buffer containing 50 mM Tris HCl, pH 7.5, 150 nM NaCl, and 0.1% polyethylene glycol 6000 was added to each sample well followed by 100 ul of 6 nM of human FXa (in assay buffer) (Enzyme Research Lab. USA). The plate was mixed in a plate shaker for about 30 seconds. The reaction was started by the addition of 50 ul of 656 uM of chromogenic substrate S2222 in assay buffer (Pharmacia Hepar Inc. USA). FXa activity was measured at 405 nM at room temperature for five minutes at 10 seconds interval in a THERMOmax microtiter plate reader (Molecular Devices). An internal standard was assayed in parallel as control. Initial rate as mOD/min was determined using OD readings in the first two minutes of the reaction. $IC_{50}$ values were determined with a 4-parameter curve fit program provided by the Molecular Devices' software, SOFTmax 2.32. Ki values were then calculated with the following equation: $Ki=IC_{50}/(1+[S]/Km)$. Km of S2222=237 uM under the present assay condition. Test results follow in Table III.

TABLE III

| COMPOUNDS | Ki (Xa) nM |
| --- | --- |
| (1) EX. 1 E,E | 27000 ± 2600 |
| (2) EX. 2 Z,Z | 3.45 ± 0.07 |
| (3) EX. 2 Z,E | 210 ± 34 |

The foregoing test results illustrate the compounds of this invention to be potent and selective inhibitors of Factor Xa. As pointed out previously such inhibition would be useful in a variety of thrombotic diseases, In general, the compounds of this invention may be administered orally which is preferred or parenterally if this is a necessary mode. The dosage of the compounds to be administered will be dependent on the age, weight, and sex of the subject and the disease to be treated. For oral formulation in solid form the compounds can be admixed with any number of suitable pharmaceutical diluents or carriers such as lactose, surcrose, starch powder, cellulose, calcium sulfate, sodium benzoate and the like. Such formulations can be compressed into tablets or can be encapsulated with gelatin capsules for convenient oral administration. The compounds could also be administered as a liquid for oral ingestions, as a solution or suspension with the necessary pharmaceutically inert/non-toxic carriers.

In certain disease states parenteral administration may be deemed a more desireable mode. For parenteral administration a compound of the invention can be formulated as an intramuscular or intravenous medicament but is not limited thereto. In certain treatments it may be desirable to administer a compound of the invention by an intravenous slow bolus in order to effect a rapid anti-coagulant effect. The normalized condition of the subject could then be maintained by oral administration of the compound.

The invention described hereinabove is illustrated below in the Examples which, however, is not to be construed as limiting the invention.

EXAMPLE 1

E,E-1,3-bis[(4'-(amino(imino)methyl)phenyl) methylene]-2-oxocycloheptane, hydrochloride.

Cycloheptanone (1.27 g) is added to a suspension of 4.2 g of 4-amidino benzaldehyde hydrochloride (G. C. Rovnyak- U.S. Pat. No. 4,325,958) in 20 mL of 85% phosphoric acid. The reaction mixture is heated to 100° C. in an oil bath for 3 h. The reaction is allowed to cool overnight. The viscous liquid is diluted with 50 mL of methanol, followed by 500 mL of ether. The product is isolated by decanting off the liquid, dissolving the residue in methanol, treating with charcoal and filtering through celite. The filtrate is diluted with ether and the resulting solid is isolated by filtration.

The material is dissolved in 20 mL of methanol and treated with anhydrous HCl gas. The solution is poured into ether (300 mL) and the resultant solid is filtered and dried in vacuo to yield the title compound.

NMR (DMSO-d$_6$) δ=1.92(s, 4H), 2.67(s, 4H), 7.35(s, 2H), 7.72(d, 4H,), 7.92(d, 4H,), 9.30(s,4), 9.50(s,4).

EXAMPLE 2

Z,E-1,3-bis[(4'-(amino(imino)methyl)phenyl) methylene]-2-oxocycloheptane, trifluoroacetate and Z,Z-1,3-bis[(4'-(amino(imino)methyl)phenyl) methylene]-2-oxocycloheptane, trifluoroacetate A solution of 0.53 g of Example 1 in 22 mL of a 5:5:1 mixture of acetonitrile:water:trifluoroacetic acid in a pyrex vessel is irradiated with a medium pressure, quartz, mercury-vapor, 450 W lamp. The irradiation is stopped after 2 h. The mixture is immediately separated on a reverse phase HPLC (Dynamax C18, 41.4 mm) using a 20–30% gradient of acetonitrile (0.1% TFA)/water (0.1% TFA). A small amount of the E,E-isomer eluted first, the Z,E isomer second and the Z,Z isomer third. The compounds are isolated by concentrating the effluent on a rotoevaporator. The residues are dissolved in methanol and treated with ether. The resulting solids are isolated by filtration and dried to give the title compounds.

Z,E - NMR (DMSO-d$_6$) δ=1.90(m, 4H), 2.51(m+DMSO, 2H), 2.79(m, 2H), 6.84(s, 1H), 7.35(d, 2H), 7.63(s,1), 7.72 (m, 4H), 7.91(d, 2H), 9.09(s, 2), 9.19(s, 2), 9.29(s, 2), 9.40(s, 2).

Z,Z - NMR (DMSO-d$_6$) δ=1.90(m, 4H), 2.58(m, 4H), 6.96(s, 2H), 7.44(d, 4H), 7.71 (d, 4H), 9.17(br m,8).

EXAMPLE 3

E,E-1,3-bis[(4'-(amino(imino)methyl)phenyl) methylene]-2-oxocyclohexane, phosphate Cyclohexanone (1.11 g) is added to a suspension of 4.2 g of 4-amidino benzaldehyde in 20 mL of 85% phosphoric acid. The reaction mixture is heated to 100° C. in an oil bath for 3 h. The reaction is allowed to cool. The viscous liquid is diluted with 50 mL of methanol. The resultant slurry is stirred for 30 min. The solid is isolated by filtration, washed with methanol and ether, and dried to give the title compound.

NMR (DMSO-d$_6$) δ=1.77(m,2), 2.94(s,4), 7.69(s,2), 7.77 (d,4), 7.95(d,4), 9.36(s,4), 9.54(s,4).

EXAMPLE 4

Z,E-1,3-bis[(4'-(amino(imino)methyl)phenyl) methylene]-2-oxocyclohexane, trifluoroacetate and Z,Z-1,3-bis[(4'-(amino(imino)methyl)phenyl) methylene]-2-oxocyclohexane, trifluoroacetate A solution of 1.0 g of the above from Example 3 in a solution of 40 mL of acetonitrile and 40 mL of water containing 0.1% trifluoroacetic acid is irradiated with a medium pressure, quartz, mercury vapor, 450 W lamp. The irradiation is stopped after 6 h. The mixture of isomers is separated on a reverse phase HPLC (Dynamax C18, 41.4 mm) using a 20–30% gradient of acetonitrile (0.1% TFA)/ water (0.1% TFA). A small amount of the E,E isomer elutes first, the Z,E isomer second, the Z,Z isomer third. The compounds are isolated by concentrating the effluent on a rotoevaporator and lyophilization. The residues are dissolved in methanol and treated with ether. The resulting solids are isolated by filtration and dried to afford the title compounds.

Z,E - NMR (DMSO-d$_6$) δ=1.84(m, 2), 2.80(m, 2), 2.92(m, 2), 6.90(s, 1), 7.42(s, 1), 7.60(d, 2), 7.75(m, 4), 7.88(d, 2), 9.13(d, 4), 9.38(d, 4).

Z,Z- NMR (DMSO-$d_6$) $\delta$=2.02(m,2), 2.82(m,4), 6.82(s, 2), 7.40(d,4), 7.64(d,4), 9.2(br m,8).

EXAMPLE 5

E,E-1-(4'-(amino(imino)methyl)phenyl)methylene-3-(4'-(aminocarbonyl)phenyl)methylene-2-oxocycloheptane, hydrochloride A mixture of 20.0 g of 4-cyanobenzaldehyde, 30.5 g of cycloheptanone, and 200 mL of 85% phosphoric acid is heated for 1.5 h at 100° C. The mixture is cooled to room temperature, and filtered. The filtrate is poured into water (800 mL), and the precipitate is filtered, washed with water, and dried. The solid is purified by flash chromatography eluting with a mixture of ether:hexane, 1:2 to afford (4-cyanophenylmethylene)cycloheptanone.

2.66 g of (4-cyanophenylmethylene)cycloheptanone is added to a suspension of 2.18 g of 4-amidinobenzaldehyde hydrochloride in 16 mL of 85% phosphoric acid. The mixture is heated for 4 h at 100° C., then cooled to 50° C. The reaction mixture is slowly added into water (75 mL) with stirring, and then allowed to stand overnight at room temperature. The solid is filtered, and washed sequentially with methanol and ether and dried in vacuo to afford 1.9 g of a solid.

The crude product is suspended in methanol (40 mL) and treated with anhydrous HCl gas until all the solid is in solution. The solution is poured into ether (300 mL) and the solid is filtered and dried in vacuo to afford the title compound.

NMR (DMSO-$d_6$) $\delta$=1.94(m,4), 2.69(m,4), 7.34(s,2), 7.46(s,1), 7.60(d,2), 7.74(d,2), 7.95(m,4), 8.10(s,1), 9.28(s, 2), 9.49(s,2).

EXAMPLE 6

Z,Z-1-(4'-(amino(imino)methyl)phenyl)methylene-3-(4'-(aminocarbonyl)phenyl)-methylene-2-oxocycloheptane, trifluoroacetate and Z,E/E,Z-1-(4'-(amino(imino)methyl)phenyl)methylene-3-(4'-(aminocarbonyl)phenyl)-methylene-2-oxocycloheptane, trifluoroacetate 0.50 g of Example 5 is dissolved in methanol (5 mL) and irradiated with a medium pressure, quartz, mercury-vapor lamp for 3 h. The solution is concentrated with a stream of nitrogen, and the residue purified by preparative reverse phase HPLC, eluting with 23% of acetonitrile (0.1% TFA) /water (0.1% TFA). The first isomer to elute is the EE-isomer (Example 9). The second component to elute is a mixture of the EZ and ZE isomers. Lyophilization affords the EZ/ZE mixture as a solid.

NMR (DMSO-$d_6$) $\delta$=1.95(m,4), 2.42(m+DMSO,2), 2.70 (m,2), 6.74(s,0.5), 6.80(s,0.5), 7.22–8.10(m,11), 9.22–9.62 (m,4).

The third isomer to elute is the ZZ-isomer. Lyophilization affords the ZZ-isomer as a solid.

NMR (DMSO-$d_6$) $\delta$=1.94(m,4), 2.60(m,4), 6.89(s, 1), 6.96(s, 1), 7.38(d, 2), 7.40(s,1), 7.45(d,2), 7.76(m,4), 7.97 (s,1), 9.03(s,2), 10.29(s,2).

EXAMPLE 7

E,E-1-(4'-(amino(imino)methyl)phenyl)methylene-3-(4'-(N'-methylamino-(imino)methyl)phenyl)methylene-2-oxocycloheptane, hydrochloride 2.00 g of (4-cyanophenylmethylene)cycloheptanone (see Ex. 5) is dissolved in a mixture of 17 mL of anhydrous ethanol and 34 mL of anhydrous dioxane. The solution is cooled to 0° C., and saturated with anhydrous HCl, while maintaining the temperature of the reaction mixture at 0°–5° C. The reaction mixture is allowed to stand for 60 h at 0°–5° C., then slowly added to 800 mL of a 3:1 mixture of ether:hexane. The solid is filtered and dried in vacuo to afford the ethyl imidate as the hydrochloride salt.

1.5 g of the above imidate is partitioned between ether and 10% aqueous sodium bicarbonate. The ether layer is dried with magnesium sulfate, and the ether is removed with a rotoevaporator. The residue is added to a solution of 0.42 g of methylamine hydrochloride in 40 mL of methanol, and the solution is heated for 3 h at 95° C. in a sealed vessel. The reaction mixture is cooled, the solvent removed with a rotoevaporator, and the residue purified by flash chromatography eluting with a 14:2:1:1 mixture of ethyl acetate: methanol:water:aqueous ammonium hydroxide to afford the N-methyl-amidine as a solid.

1.24 g of the N-methyl-amidine from above is added to a mixture of 0.94 g of 4-amidinobenzaldehyde in 15 mL of 85% phosphoric acid. The mixture is heated for 3.5 h at 100° C., then cooled to room temperature. The reaction mixture is then diluted with 20 mL of methanol and slowly added to a stirring ether solution. The mixture is allowed to stand for 18 h at room temperature. The solvent is poured off, and the residue is taken up in 25 mL of a methanol/HCl(g) solution. The solution is poured into ether (300 mL) and the solid is filtered and dried in vacuo to afford the title compound.

NMR (DMSO-$d_6$) $\delta$=1.96(m,4), 2.67(m,4), 3.02(m,3), 7.39(s,2), 7.70–7.92(m,8), 9.02(s,1), 9.27(s,2), 9.39(s,2), 9.55(s,1), 9.85(m,1).

EXAMPLE 8

Z,Z-1-(4'-(amino(imino)methyl)phenyl)methylene-3-(4'-(N'-methylamino-(imino)methyl)phenyl)methylene-2-oxocycloheptane, trifluoroacetate and Z,E/E,Z-1-(4'-(amino(imino)methyl)phenyl)methylene-3-(4'-(N'-methylamino (imino)methyl)phenyl)methylene-2-oxocycloheptane, trifluoroacetate 0.27 g of Example 7 is dissolved in methanol (55 mL) and irradiated with a medium pressure, quartz, mercury-vapor lamp for 3 h. The solution is concentrated with a rotoevaporator, and the residue purified by preparative reverse phase HPLC, eluting with 20% of acetonitrile (0.1% TFA)/water (0.1% TFA). The first isomer to elute is the EE-isomer. The second isomer component to elute is a mixture of the EZ and ZE isomers. Lyophillization affords the EZ/ZE mixture as a solid.

NMR (DMSO-$d_6$) $\delta$=1.92(m,4), 2.55(m+DMSO,2), 2.71 (m,2), 3.02(m,3), 6.82(s,1 ), 7.40–7.95(m,9), 8.95–9.95(m, 7).

The third isomer to elute is the ZZ-isomer. Lyophilization affords the ZZ-isomer as a solid.

NMR (DMSO-$d_6$) $\delta$=1.95(m,4), 2.58(m,4), 3.02(m,3), 6.98(s,2), 7.45(m,4), 7.65(m,2), 7.73(m,2), 8.92(s,1), 9.15 (s,2), 9.34(s,2), 9.42(s, 1), 9.78(m,1).

EXAMPLE 9

E,E-1-(4'-(amino(imino)methyl)phenyl)methylene-3-(4'-(N',N'-dimethylamino (imino)methyl)phenyl)methylene-2-oxocycloheptane 2.00 g of (4-cyanophenylmethylene)cycloheptanone (see Ex. 5) is dissolved in a mixture of 17 mL of anhydrous ethanol and 34 mL of anhydrous dioxane. The solution is cooled to 0° C., and saturated with anhydrous HCl, while maintaining the temperature of the reaction mixture at 0°–5° C. The reaction mixture is allowed to stand for 60 h at 0°–5° C., then slowly added to 800 mL of a 3:1 mixture of ether:hexane. The solid is filtered and dried in vacuo to afford the ethyl imidate as the hydrochloride salt.

1.75 g of the above imidate is partitioned between ether and 10% aqueous sodium bicarbonate. The ether layer is dried with magnesium sulfate, and the ether is removed with a rotoevaporator. The residue is added to a solution of 0.54 g of dimethylamine hydrochloride in 40 mL of methanol, and the solution is heated for 3 h at 90° C. in a sealed vessel. The reaction mixture is cooled, the solvent removed with a rotoevaporator to afford the crude N,N-dimethylamidine as an oil.

1.1 g of the N,N-dimethylamidine from above is added to a mixture of 1.0 g of 4-amidinobenzaldehyde in 15 mL of 85% phosphoric acid. The mixture is heated for 3.5 h at 100° C., then cooled to room temperature. The reaction mixture is then diluted with 20 mL of methanol and slowly added to a stirring ether solution. The mixture is allowed to stand for 18 h at room temperature. The solvent is poured off, and the residue is taken up in 25 mL of a methanol/HCl (g) solution. The solution is poured into ether (300 mL) and the residue is purified by preparative reverse phase HPLC, eluting with a gradient of 15–30% of acetonitrile (0.1% TFA) / water (0.1% TFA). Lyophilization affords the title compound.

NMR (DMSO-$d_6$) $\delta$=1.90(m,4), 2.65(m,4), 3.02(s,3), 3.25(s,3), 7.38(s,2), 7.75(m,6), 7.95(d,2), 9.12(s,1), 9.38–9.62(m,5).

EXAMPLE 10

Z,Z-1-(4'-(amino(imino)methyl)phenyl)methylene-3-(4'-(N',N'-dimethylamino (imino)methyl)phenyl)methylene-2-oxocycloheptane 0.2 g of the above Example 9 is dissolved in methanol (20 mL) and irradiated with a medium pressure, quartz, mercury-vapor lamp for 3 h. The solution is concentrated with a rotoevaporator, and the residue purified by preparative reverse phase HPLC, eluting with 20% of acetonitrile (0.1% TFA)/water (0.1% TFA). The major isomer to elute is the ZZ-isomer. Lyophilization affords the title compound.

NMR (DMSO-$d_6$) $\delta$=1.97(m,4), 2.61(m,4), 2.98(s,3), 3.22(s,3), 6.95(s,1), 7.00(s,1), 7.65(m,6), 7.76(d,2), 8.93(s,1), 9.2–9.4(m,5).

EXAMPLE 11

Z,Z-3,5-bis[(4'-(amino(imino)methyl)phenyl)methylene]-4-oxocyclohexanoic acid, trifluoroacetate A solution of 0.25 g of E,E-3,5-bis[(4'-(amino(imino)methyl)phenyl)methylidene]-4-oxocyclohexanoic acid hydrochloride (G. C. Rovnyak, U.S. Pat. No. 4,341,797), in water (5 mL) is irradiated with a medium pressure, quartz, mercury-vapor lamp for 1 h. The solution is purified by reverse phase HPLC eluting with a 18–28% gradient of acetonitrile (0.1% TFA)/water (0.1% TFA). The major isomer to elute is the ZZ-isomer. Lyophillization affords the ZZ isomer as a solid.

NMR (DMSO-$d_6$) $\delta$=3.05(m,5), 6.94(s,2), 7.42(d,4), 7.65 (d,4), 9.18(s,4), 9.32(s,4).

EXAMPLE 12

E,E-1,3-bis[(3'-(amino(imino)methyl)phenyl)methylene]-2-oxocycloheptane, dihydrochloride 0.70 g of cycloheptanone is added to a suspension of 2.32 g of 3-amidinobenzaldehyde (G. C. Rovnyak, U.S. Pat. No. 4,325,958) in 12 mL of 85% phosphoric acid. The mixture is heated for 3.5 h at 100° C., then cooled to room temperature. The dark red reaction mixture is diluted with 20 mL of methanol, and to this solution is added 75 mL of ether over 5 min. The product that separates is filtered, and washed with methanol/ethyl acetate (1:1) and dried in vacuo to afford 1.2 g of a solid.

The crude product is suspended in methanol and treated with anhydrous HCl gas for 5 min. The solution is allowed to cool and left overnight at room temperature. The product is collected to afford the title compound.

NMR (DMSO-$d_6$) $\delta$=1.95(m,4), 2.71(m,4), 7.33(s,2), 7.70–7.87(m,6), 7.93(s,2), 9.38(s,4), 9.53(s,4).

EXAMPLE 13

Z,Z-1,3-bis[(3'-(amino(imino)methyl)phenyl)methylene]-2-oxocycloheptane, trifluoroacetate and Z,E-1,3-bis[(3'-(amino(imino)methyl)phenyl)methylene]-2-oxocycloheptane, trifluoroacetate 0.40 g of Example 12 is dissolved in methanol (500 mL) and irradiated with a 150 watt flood light for 14 days. The methanol is removed with a rotoevaporator, and the residue purified by preparative reverse phase HPLC, eluting with a 15–22% gradient of acetonitrile (0.1% TFA)/water (0.1% TFA). The first isomer to elute is the EE-isomer. The second isomer to elute is the ZE-isomer. Lyophilization affords the ZE isomer as a solid.

NMR (DMSO-$d_6$) $\delta$=1.92(m,4), 2.50(m+DMSO,2), 2.76 (m,2), 6.80(s,1), 7.50–7.90(m,9), 9.19(d,4), 9.38(d,4).

The third isomer to elute is the ZZ-isomer. Lyophilization affords the ZZ-isomer as a solid.

NMR (DMSO-$d_6$) $\delta$=1.92(m,4), 2.62(m,4), 6.95(s,2), 7.46–7.86(m,8), 9.23(s,4), 9.38(s,4).

EXAMPLE 14

Z,E-1,3-bis[(4'-amino(imino)methyl)phenyl)methylene]-2-oxocyclodecane and

Z,Z-1,3-bis[(4'-amino(imino)methyl)phenyl)methylene]-2-oxocyclodecane

Cyclodecanone (0.77 g) is added to a suspension of 2.0 g of 4-amidino benzaldehyde in a mixture of 8 mL of water and 2 mL of hydrochloric acid. The reaction was heated at 100° C. for 3 days and allowed to cool over 10 h. The slurry is concentrated, dissolved in methanol, treated with charcoal, filtered through celite and precipitated with ether. The mixture is separated on a reverse phase HPLC (Dynamax C18, 41.4 mm) using a gradient of 20–75% acetonitrile (0.1% TFA)/water (0.1% TFA). The compound is isolated by concentrating the effluent on a rotoevaporator. The residue is dissolved in methanol and treated with ether. The resulting solid was isolated by filtration and dried.

A solution of approximately 0.5 g of the previous compound in 15 mL of a 2 to 1 mixture of acetonitrile and water, respectively, containing 0.1% trifuluoroacetic acid is placed in a glass flask next to a medium pressure, quartz, mercury vapor, 450 W lamp. The sample is irradiated for 10 h to yield a mixture of isomers. The mixture is separated on a reverse phase HPLC (Dynamax C18, 41.4 mm) using 30% acetonitrile (0.1% TFA)/water (0.1% TFA). The compounds are isolated by concentrating the effluent on a rotoevaporator. The residue is dissolved in methanol and treated with ether. The resulting solids are isolated by filtration and dried to give the title compounds.

Z,E NMR (DMSO-$d_6$) δ=1.5(m, 10H), 2.6(m +DMSO, 2H), 2.82(m, 2H), 7.05(s, 1H), 7.47(m,3), 7.65(d,2), 7.75(d, 2), 7.86(d,2), 9.19(s,2), 9.27(s,2), 9.36(s,2).

Z,Z NMR (DMSO-$d_6$) δ=1.36(m, 4H), 1.55(m, 6H), 2.35 (m, 4H), 6.96(s, 2H), 7.56(d,4), 7.77(d,4), 9.10(s,4), 9.33(s, 4).

EXAMPLE 15

Z,E-1,3-bis[(4'-(amino(imino)methyl)phenyl) methylene]-2-oxocyclooctane and

Z,Z-1,3-bis[(4'-(amino(imino)methyl)phenyl) methylene]-2-oxocyclooctane

Cyclooctanone (0.34 g) is added to a suspension of 1.0 g of 4-amidino benzaldehyde hydrochloride in a mixture of 4 mL of water and 1 mL of hydrochloric acid. The reaction is heated at 100° C. for 8 h and allowed to cool over 10 h. The slurry is concentrated, dissolved in methanol, treated with charcoal, and filtered through celite. The product is precipatated with the addition of 1N hydrochloric acid and purified by chromatography on a reverse phase HPLC (Dynamax C18, 41.4 mm) using 30% acetonitrile (0.1% TFA)/water (0.1% TFA). A small amount of the E,E isomer elutes first, the Z,E isomer second and the Z,Z isomer third. The compounds are isolated by concentrating the effluent on a rotoevaporator. The residues are dissolved in methanol and treated with ether. The resulting solids are isolated by filtration and added to give the title compound.

Z,E - NMR (DMSO, TMS) δ=1.57(m, 2H), 1.70(m, 4H), 2.56(m, 4H), 6.70(s, 1H), 7.37(d,2), 7.64(m,3), 7.77(d,2), 7.87(d,2), 9.29(s,2), 9.40(s,2) 9.49(s,2), 9.58(s,2).

Z,Z - NMR (DMSO, TMS) δ=1.60(m, 2H), 1.71(m, 4H), 2.53(m+DMSO, 4H), 6.83(s, 2H), 7.49(d,4), 7.74(d,4), 9.12 (br s,4), 9.31(br s,4)

EXAMPLE 16

Z,E-1,3-bis[(4'-(amino(imino)methyl)phenyl) methylene]-2-oxocyclononane and

Z,Z-1,3-bis[(4'-(amino(imino)methyl)phenyl) methylene]-2-oxocyclononane

Cyclononanone (0.58 g) is added to a suspension of 2.0 g of 4-amidino benzaldehyde hydrochloride in a mixture of 8 mL of water and 2 mL of hydrochloric acid. The reaction is heated at 100° C. for 6 days and allowed to cool over 10 h. The slurry is concentrated, dissolved in methanol, treated with charcoal, filtered through celite, and precipitated with ether. The mixture is purified by chromatography on a reverse phase HPLC (Dynamax C18, 41.4 mm) using 30% acetonitrile (0.1% TFA)/water (0.1% TFA). A small amount of the E,E isomer elutes first, the Z,E isomer is second and the Z,Z isomer is third. The compounds are isolated by concentrating the effluent on a rotoevaporator. The residues are dissolved in methanol and treated with ether. The resulting solids are isolated by filtration and dried to give the title compound.

Z,E - NMR (DMSO, TMS) δ=1.8(m, 6H), 2.45(m, 2H), 2.63(m, 2H), 6.86(s, 1H), 7.45(d,2), 7.52(s,1), 7.63(d,2), 7.77(d,2), 7.84(d,2), 8.3(m,8).

Z,Z - NMR (DMSO, TMS) δ=1.56(m, 4H), 1.68(m, 2H), 2.43(m, 4H), 6.86(s, 2H), 7.49(d,4), 7.73(d,4), 9.17(s,4), 9.31(s,4).

We claim:

1. A compound of one of the following formulae:

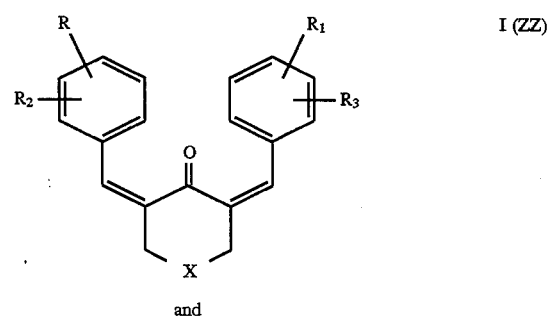

I (ZZ)

and

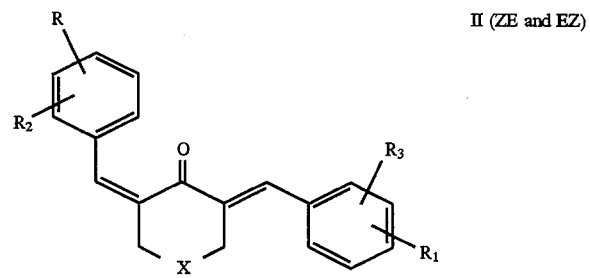

II (ZE and EZ)

wherein

R, $R_1$ are the same or independently

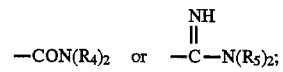

$R_2$, $R_3$ are the same or independently hydrogen, loweralkyl or halogen;

$R_4$ are the same or independently hydrogen, loweralkyl, aryl or arylloweralkyl;

$R_5$ are the same or independently hydrogen, loweralkyl, aryl, arylloweralkyl

$R_6$ is loweralkyl, aryl or arylloweralkyl;

X is $(CHR_7)_n$, O, S, SO, $SO_2$ or $NR_8$;

$R_7$ is independently hydrogen, —COOH or $(-CH_2)_p$—COOH;

$R_8$ is hydrogen, loweralkyl, arylloweralkyl or

—C—Y;

Y is loweralkyl or aryl;

n is the integers 1, 2, 3, 4 or 5;

p is the integers 1, 2, 3 or 4 and the pharmaceutically acceptable salts thereof;

with the provisos:
  a) both R and $R_1$ must be in the meta or para positions,
  b) R and $R_1$ cannot both be —CON($R_4$)$_2$,
  c) only one of $R_5$ can be

—C—$R_6$ and
  d) only one of $R_7$ can be —COOH or (—CH$_2$)$_p$—COOH.

2. A compound of claim 1, Formula I wherein R and $R_2$ are both in the para position.

3. A compound of claim 2 which is Z,Z-1,3bis[(4'-(amino(imino)methyl)phenyl)methylene]-2-oxocyclohexane, trifluoroacetate.

4. A compound of claim 2 which is Z,Z-3,5-bis[(4'-(amino(imino)methyl)phenyl)methylene]-4-oxocyclohexanoic acid.

5. A compound of claim 2 which is Z,Z-1,3-bis[(4'-(amino(imino)methyl)phenyl)methylene]-2-oxocycloheptane.

6. A compound of claim 2 which is Z,Z-1-(4'-(amino(imino)methyl)phenyl)methylene-3-(4'-(aminocarbonyl)phenyl)methylene-2-oxocycloheptane.

7. A compound of claim 2 which is Z,Z-1-(4'-(N'-methylamino(imino)methyl)phenyl)methylene-2-oxocycloheptane.

8. A compound of claim 2 which is Z,Z-1-(4'-(amino(imino)methyl)phenyl)methylene-3-(4'-(N',N'-dimethylamino(imino)methyl)phenyl)methylene-2-oxocycloheptane.

9. A compound of claim 2 which is Z,Z-1,3-bis[(4'-(amino(imino)methyl)phenyl)methylene]-2-oxocyclooctane.

10. A compound of claim 2 which is Z,Z-1,3-bis[(4'-(amino(imino)methyl)phenyl)methylene]-2-oxocyclononane.

11. A compound of claim 2 which is Z,Z-1,3-bis[(4'-amino(imino)methyl)phenyl)methylene]-2-oxocyclodecane.

12. A compound of claim 1, Formula I wherein R and $R_1$ are both in the meta position.

13. A compound of claim 12, which is Z,Z-1,3-bis[(3'-(amino(imino)methyl)phenyl)methylene]-2-oxocycloheptane.

14. A compound of claim 1, Formula II wherein R and $R_1$ are both in the para position.

15. A compound of claim 14 which is Z,E-1,3-bis[(4'-(amino(imino)methyl)phenyl)methylene]-2-oxocyclohexane.

16. A compound of claim 14 which is Z,E-1,3-bis[(4'-(amino(imino)methyl)phenyl)methylene]-2-oxocycloheptane.

17. A compound of claim 14 which is Z,E-1,3-bis[(4'-(amino(imino)methyl)phenyl)methylene]-2-oxocyclooctane.

18. A compound of claim 14 which is Z,E-1,3-bis[(4'-(amino(imino)methyl)phenyl)methylene]-2-oxocyclononane.

19. A compound of claim 14 which is Z,E-1,3-bis[(4'-amino(imino)methyl)phenyl)methylene]-2-oxocyclodecane.

20. A compound of claim 1, Formula II wherein R and $R_1$ are both in the meta position.

21. A compound of claim 20 which is Z,E-1,3-bis[(3'-(amino(imino)methyl)phenyl)methylene]-2-oxocycloheptane.

22. A method of inhibiting Factor Xa in a mammalian host in need thereof, which comprises administering to said host an effective amount of a compound of claim 1.

23. A pharmaceutical composition comprising a therapeutically effective amount of at least one compound according to claim 1, together with one or more non-toxic pharmaceutically acceptable carriers.

* * * * *